(12) United States Patent
Rodger et al.

(10) Patent No.: US 11,122,975 B2
(45) Date of Patent: Sep. 21, 2021

(54) IMPLANTABLE EXTRACOMPARTMENTAL PRESSURE SENSOR

(71) Applicants: California Institute of Technology, Pasadena, CA (US); University of Southern California, Los Angeles, CA (US)

(72) Inventors: Damien C. Rodger, Venice, CA (US); Yu-Chong Tai, Pasadena, CA (US); Mark S. Humayun, Glendale, CA (US); Aubrey M. Shapero, Pasadena, CA (US); Abhinav Agarwal, Pasadena, CA (US); Azita Emami, Pasadena, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 564 days.

(21) Appl. No.: 15/948,187

(22) Filed: Apr. 9, 2018

(65) Prior Publication Data

US 2018/0325373 A1    Nov. 15, 2018

Related U.S. Application Data

(60) Provisional application No. 62/505,541, filed on May 12, 2017.

(51) Int. Cl.
*A61B 3/16*       (2006.01)
*A61F 9/007*      (2006.01)
(Continued)

(52) U.S. Cl.
CPC ............ *A61B 3/16* (2013.01); *A61F 9/00781* (2013.01); *A61M 1/84* (2021.05);
(Continued)

(58) Field of Classification Search
CPC .............. A61B 3/16; A61B 2562/0247; A61B 2562/168; A61B 2562/166;
(Continued)

(56) References Cited

U.S. PATENT DOCUMENTS

| 3,341,794 A | 9/1967 | Stedman |
| 3,838,684 A | 10/1974 | Manuel et al. |

(Continued)

FOREIGN PATENT DOCUMENTS

| CN | 2366109 Y | 3/2000 |
| CN | 101032400 A | 9/2007 |

(Continued)

OTHER PUBLICATIONS

Cong et al., "Wireless Implantable Blood Pressure Sensing Microsystem Design for Monitoring of Small Laboratory Animals", Sensors and Materials, vol. 20, Issue 7, 2008, pp. 327-340.

(Continued)

*Primary Examiner* — Sean P Dougherty
(74) *Attorney, Agent, or Firm* — Kilpatrick Townsend & Stockton LLP

(57) ABSTRACT

A miniature, low power electronic pressure sensor with a first, oil-filled chamber to protect its microelectromechanical systems (MEMS) pressure sensitive membrane and a second chamber filled with saline or body fluids connected by tube into an organ in the body, such as an eyeball, that needs pressure sensing, is described. The tube carries pressure from a sensitive area within the organ to the electronic pressure sensor. The pressure sensor may communicate wirelessly with external readers and pass data to a server or other computer. Running alongside the tube is another tube for draining and pressure relief. The tubes, or cannulas, can share an opening into the organ in order to minimize the number of holes needed. The tubes may be molded into a (Continued)

single oval cross section, combined coaxially, or share a lumen for a portion that enters the wall of an organ so as to promote healing.

20 Claims, 8 Drawing Sheets

(51) Int. Cl.
*A61M 1/00* (2006.01)
*A61M 27/00* (2006.01)

(52) U.S. Cl.
CPC ... *A61B 2562/0247* (2013.01); *A61B 2562/12* (2013.01); *A61B 2562/166* (2013.01); *A61B 2562/168* (2013.01); *A61M 27/00* (2013.01); *A61M 2205/04* (2013.01); *A61M 2210/0612* (2013.01)

(58) Field of Classification Search
CPC ... A61F 9/00781; A61M 1/008; A61M 27/00; A61M 2210/0612; A61M 2205/04
See application file for complete search history.

(56) References Cited

U.S. PATENT DOCUMENTS

| | | | |
|---|---|---|---|
| 4,264,889 A | 4/1981 | Yamamoto et al. | |
| 4,519,401 A | 5/1985 | Leung et al. | |
| 4,586,018 A | 4/1986 | Bettman | |
| 4,604,900 A | 8/1986 | Knudsen et al. | |
| 4,662,226 A | 5/1987 | Wang et al. | |
| 4,846,191 A | 7/1989 | Brockway et al. | |
| 5,535,752 A | 7/1996 | Halperin et al. | |
| 6,010,461 A | 1/2000 | Haniff et al. | |
| 6,134,970 A | 10/2000 | Kumakawa et al. | |
| 6,148,673 A | 11/2000 | Brown | |
| 6,221,024 B1* | 4/2001 | Miesel | A61B 5/0215 600/486 |
| 6,439,055 B1 | 8/2002 | Maron et al. | |
| 8,313,811 B2 | 11/2012 | Hogg et al. | |
| 8,313,819 B2 | 11/2012 | Hogg et al. | |
| 8,361,591 B2 | 1/2013 | Hogg et al. | |
| 8,529,538 B2 | 9/2013 | Pang et al. | |
| 8,603,024 B2 | 12/2013 | Bohm et al. | |
| 8,764,685 B2 | 7/2014 | Casey | |
| 8,926,510 B2 | 1/2015 | Marshall et al. | |
| 2001/0045509 A1 | 11/2001 | Al-Ali et al. | |
| 2002/0073783 A1 | 6/2002 | Wilner et al. | |
| 2004/0020300 A1 | 2/2004 | Boehler et al. | |
| 2004/0073122 A1 | 4/2004 | Stofer et al. | |
| 2004/0162545 A1* | 8/2004 | Brown | A61F 9/00781 604/541 |
| 2004/0176672 A1 | 9/2004 | Silver et al. | |
| 2005/0288596 A1 | 12/2005 | Eigler et al. | |
| 2006/0071286 A1 | 4/2006 | Axelrod et al. | |
| 2006/0189887 A1* | 8/2006 | Hassler, Jr. | A61F 5/0003 600/561 |
| 2006/0189917 A1* | 8/2006 | Mayr | A61F 9/00781 604/9 |
| 2006/0211914 A1* | 9/2006 | Hassler, Jr. | A61F 5/0003 600/37 |
| 2007/0118038 A1 | 5/2007 | Bödecker et al. | |
| 2007/0243230 A1* | 10/2007 | de Juan, Jr. | A61L 31/16 424/427 |
| 2008/0139959 A1 | 6/2008 | Miethke et al. | |
| 2010/0312188 A1 | 12/2010 | Robertson et al. | |
| 2011/0066046 A1 | 3/2011 | Young et al. | |
| 2011/0071454 A1* | 3/2011 | Dos Santos | A61F 9/00781 604/8 |
| 2011/0071456 A1* | 3/2011 | Rickard | A61B 5/6821 604/9 |
| 2011/0071458 A1* | 3/2011 | Rickard | A61P 27/06 604/9 |
| 2011/0071459 A1* | 3/2011 | Rickard | A61F 9/00781 604/9 |
| 2011/0132097 A1 | 6/2011 | Hegner et al. | |
| 2011/0160560 A1 | 6/2011 | Stone et al. | |
| 2011/0271764 A1 | 11/2011 | Lee et al. | |
| 2011/0296925 A1 | 12/2011 | Miesel et al. | |
| 2012/0197231 A1 | 8/2012 | Kane et al. | |
| 2012/0247227 A1* | 10/2012 | Crivelli | G01L 19/149 73/862.381 |
| 2013/0062713 A1 | 3/2013 | Sakuragi et al. | |
| 2013/0137958 A1 | 5/2013 | Tai et al. | |
| 2013/0150776 A1* | 6/2013 | Bohm | A61B 3/16 604/9 |
| 2013/0233086 A1 | 9/2013 | Besling et al. | |
| 2014/0005569 A1 | 1/2014 | Miethke et al. | |
| 2014/0171777 A1* | 6/2014 | Sanchez | A61F 9/00781 600/398 |
| 2014/0296687 A1 | 10/2014 | Irazoqui et al. | |
| 2015/0057595 A1 | 2/2015 | Gunn et al. | |
| 2016/0235296 A1 | 8/2016 | Dunning | |
| 2016/0235298 A1 | 8/2016 | Gunn | |
| 2016/0249818 A1* | 9/2016 | Philipp | A61B 5/02141 600/486 |
| 2016/0287101 A1 | 10/2016 | Tai et al. | |
| 2016/0349162 A1* | 12/2016 | Ebert | G01N 33/49 |
| 2017/0014270 A1* | 1/2017 | Tyler | A61F 9/00781 |
| 2017/0095163 A1* | 4/2017 | Bitzer | A61B 5/686 |

FOREIGN PATENT DOCUMENTS

| | | |
|---|---|---|
| CN | 200942206 Y | 9/2007 |
| CN | 102202719 | 9/2011 |
| CN | 203620057 U | 6/2014 |
| CN | 104010568 | 8/2014 |
| CN | 107529985 | 1/2018 |
| DE | 102004056757 | 6/2006 |
| EP | 1312302 | 5/2003 |
| JP | 2008539811 | 11/2008 |
| JP | 2010503220 | 1/2010 |
| JP | 2013545973 | 12/2013 |
| JP | 2014208301 | 11/2014 |
| WO | 03094693 | 11/2003 |
| WO | 2005022110 | 3/2005 |
| WO | 2008140395 | 11/2008 |
| WO | 2011035262 | 3/2011 |
| WO | 2013003754 A1 | 1/2013 |
| WO | 2014055989 | 4/2014 |
| WO | 2014195372 | 12/2014 |
| WO | 2016160402 | 10/2016 |

OTHER PUBLICATIONS

PCT/US2016/023454, "International Search Report and Written Opinion", dated Jun. 27, 2016, 17 pages.
Shapero, et al., "Parylene-Oil-Encapsulated Low-Drift Implantable Pressure Sensors", The 31st IEEE International Conference on Micro Electro Mechanical Systems (MEMS 2018), Belfast, Northern Ireland, UK, Jan. 21-25, pp. 47-50.
U.S. Appl. No. 15/076,184, "Restriction Requirement", dated Jul. 27, 2018, 7 pages.
PCT/US2018/026705, "International Search Report and Written Opinion Received", dated Jun. 18, 2018, 8 pages.
Binh-Khiem et al., "Tensile Film Stress of Parylene Deposited Liquid", Langmuir Article, vol. 26, No. 24, Nov. 16, 2010, pp. 18771-18775.
Hogg, "Development and Characterisation of Ultrathin Layer Packaging for Implantable Medical Devices", PhD Thesis, University of Applied Sciences, Sep. 5, 2014, 219 pages.
PCT/US2016/023454, "International Preliminary Report on Patentability", dated Oct. 12, 2017, 15 pages.
PCT/US2018/026705, "International Preliminary Report on Patentability", dated Nov. 21, 2019, 7 pages.
Wacker-Chemie GmbH, "Silicone Fluids AK," Jan. 2002.
U.S. Appl. No. 15/076,184, "Final Office Action", dated Feb. 15, 2019, 12 pages.

(56) References Cited

OTHER PUBLICATIONS

U.S. Appl. No. 15/076,184, "Non-Final Office Action", dated Sep. 7, 2018, 10 pages.
CN201680027137.3, "Office Action", dated Dec. 4, 2018, 8 pages.
Cong et al., "Implantable Blood Pressure Monitoring of Small Animal for Advanced Biological Research", The 13th International Conference on Solid-State Sensors, Actuators and Microsystems, 2005. Digest of Technical Papers. Transducers '05, IEEE, vol. 2, 2005.
EP16773748.5, "Extended European Search Report", dated Nov. 23, 2018, 7 pages.
Wheeler et al., "MEMS-Based Bubble Pressure Sensor for Prosthetic Socket Interface Pressure Measurement", Annual International Conference of the IEEE Engineering in Medicine and Biology Society, 2011, pp. 2925-2928.
EP18798545.2, "Extended European Search Report", dated Dec. 9, 2020, 5 pages.

\* cited by examiner

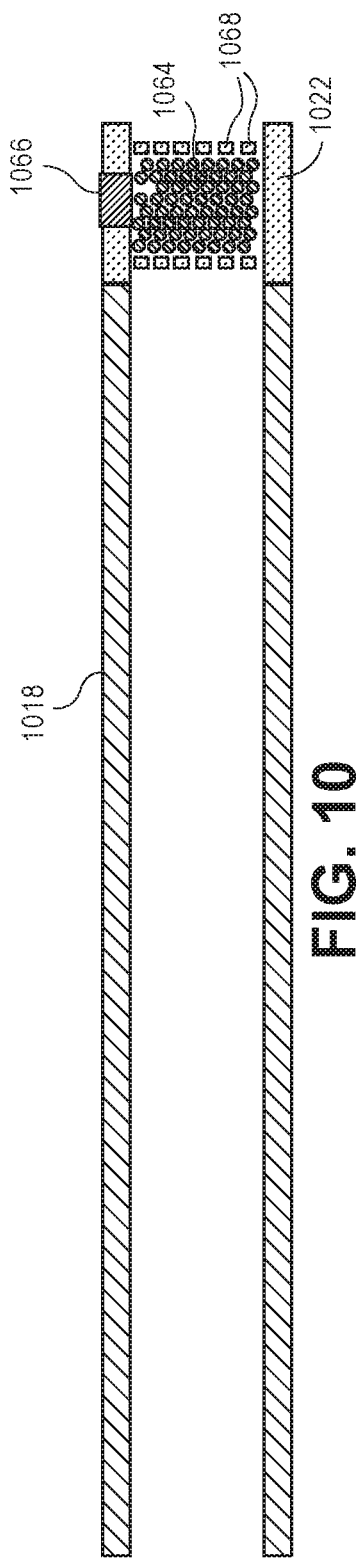
FIG. 10
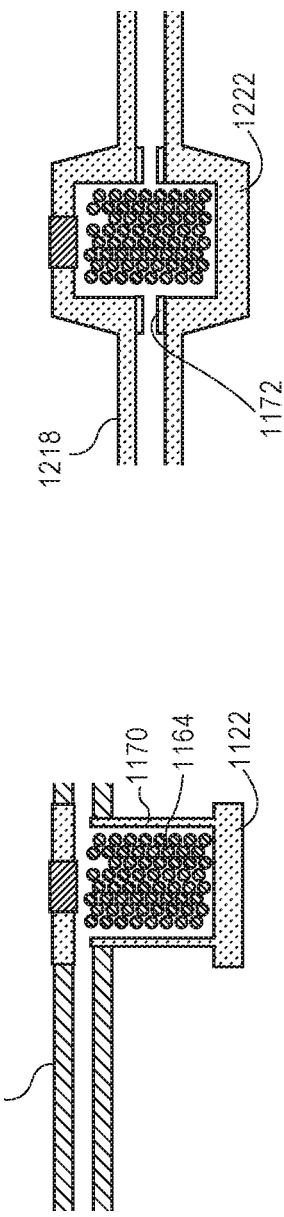
FIG. 11
FIG. 12

IMPLANTABLE EXTRACOMPARTMENTAL PRESSURE SENSOR

CROSS-REFERENCES TO RELATED APPLICATIONS

This application claims the benefit of U.S. Provisional Patent Application No. 62/505,541, filed May 12, 2017, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Art

Embodiments of the present invention generally relate to pressure sensors for measuring the pressure within the interior of cavities within a patient's body, including implantable electronic sensors for measuring intraocular pressure (IOP) within an eyeball, the implantable sensor assisting the maintenance of a pressure relief device.

2. Description of the Related Art

Glaucoma is the second leading cause of blindness, affecting 60 million people across the globe. A major risk factor for glaucoma is increased intraocular pressure (IOP), which damages the optic nerve and leads to blindness. The current standard of care for monitoring IOP is Goldmann applanation tonometry, in which patients visit the doctor's office regularly to register a single measurement per visit. It is known that IOP fluctuates throughout the day, and infrequent measurements can miss elevated IOP spikes, leading to inaccurate assessments.

A continuous, implantable IOP monitor is desired for an accurate diagnosis, to monitor treatment, and to avoid preventable permanent vision loss.

Due to sensor drift caused by chemo-biological factors such as hydrolytic corrosion and biofouling, implantable IOP sensors have difficulty reliably maintaining a clinical accuracy target of <2 mmHg for more than one month without recalibration. Such a short lifetime has rightfully prevented the use of IOP monitoring implants.

U.S. Patent Publication No. 2016/0287101 A1 to Tai et al. discloses an implantable sensor package that separates bodily fluid from a sensing membrane by encompassing the sensing membrane with liquid. This sensor package design shows excellent promise in extending the mean time between failure (MTBF) and lifetime of implantable pressure sensors.

Measuring pressure is half of the story. Relieving pressure is the other half. Tube shunts can be implanted in order to relieve pressure. Yet tubes used to drain intraocular fluid and relieve pressure from eyes also are subject to frequent biofouling. Because of biofouling, multiple tubes are sometimes implanted so that if one clogs then there is another that may be clear.

Improved devices and methods are desired for measuring IOP and relieving IOP from a patent's eye.

BRIEF SUMMARY

Generally, presented herein relates to an miniature implantable pressure sensor with an oil-filled bag or other pliable membrane protecting its membrane sensor. The pressure sensor is mounted to the outside of an eyeball's sclera, and a tube (cannula) runs from the pressure sensor into the eyeball through the pars plana. Meanwhile, a drainage tube (cannula) runs alongside the pressure tube into the eyeball, sharing the surgical slit into the pars plana. The drainage tube has a flow restrictor outside the eye that is readily serviceable by an ophthalmologist.

Other organs besides eyes can be serviced. For example, the bladder, brain, aorta, or other organs can have the implantable pressure sensor mounted outside of it and sensor and drainage tube entering them.

In the area where the tubes pass through the surgical slit, the pressure and drainage tubes can be coaxial, share a common tube, or be conformed with wedges to create a smooth, ovoid cross section. An injection port on the flow restrictor can allow a doctor's needle to fill it with microbeads.

Some embodiments of the present invention are related to an implantable pressure sensor apparatus. The apparatus includes an electronic pressure sensor with a pressure sensitive membrane, an oil chamber encapsulating the pressure sensitive membrane, the oil chamber filled with a biocompatible oil and having a pliable membrane on at least one side, a saline chamber on an opposite side of the pliable membrane from the oil chamber, a sensing cannula with a lumen extending into the saline chamber, a drain cannula with a portion adjoining and running parallel with the sensing cannula, and a flow restrictor within the drain cannula.

The apparatus can include filler wedges within valleys between the sensing cannula and the adjoining drain cannula, the filler wedges, sensing cannula, and drain cannula forming an oval cross section. The filler wedges can extend to an end of the adjoining drain cannula and sensing cannula. The end can be slanted. The filler wedges can be cured silicone rubber.

The flow restrictor can be proximate a free end of the drain cannula opposite an end with the portion adjoining and running parallel. The sensing cannula and the drain cannula can be coaxial with one another at the portion adjoining and running parallel. The sensing cannula and the drain cannula can intersect (e.g., in a "Y" or "T" junction) into a common cannula with a common lumen.

There can be microbeads within the flow restrictor, a packing of the microbeads configured to limit fluid flow. There can be an injection port on the flow restrictor configured to allow access by a needle to the microbeads. Alternatively or in conjunction, the flow restrictor can include a mechanical valve.

The apparatus can further include a flexible printed circuit board (PCB), a coil connected with the PCB, a wireless transmitter connected with the coil, and an integrated circuit (IC) configured to transmit a pressure reading from the electronic pressure sensor through the wireless transmitter and coil.

The biocompatible oil can be silicone oil, which is silicon (Si) compatible. Silicone oil is often superior to silicone gel because the latter absorbs water vapor, and water causes corrosion. The pliable membrane can be made of parylene. A glass plate can be suspended above the pliable membrane. The saline chamber can be made of a semi-rigid polymer.

Some embodiments are related to a method for manufacturing an implantable pressure sensor apparatus. The method includes removing a cover of an electronic pressure sensor to expose a pressure sensitive silicon membrane within a recess, filling the recess around the pressure sensitive silicon membrane with oil, depositing parylene on a surface of the oil to form a pliable membrane, the pliable membrane forming a side of an oil filled chamber, and fitting a cover with a tube over the pliable membrane to create a saline chamber and a sensing cannula.

A drain cannula can adjoin and run parallel with the sensing cannula. The drain cannula can include a flow restrictor. The method can further include surgically attaching the implantable pressure sensor apparatus to an eyeball, and inserting ends of the sensing cannula and the drain cannula through a slit in a pars plana of the eyeball.

BRIEF DESCRIPTION OF THE DRAWINGS

FIG. 10 illustrates a flow resistor with caged microbeads in accordance with an embodiment.

FIG. 11 illustrates a flow resistor with a step trap for microbeads in accordance with an embodiment.

FIG. 12 illustrates a flow resistor with a reduced inner diameter for trapping microbeads in accordance with an embodiment.

DETAILED DESCRIPTION

Here described is an implementation of a system for long term pressure monitoring and recording using an implantable pressure sensor in a body, such as for intraocular pressure (IOP) monitoring. The pressure at the open end of a cannula is measured by a pressure sensor that resides in a chamber well inside the device. This allows pressure to be sensed in locations too small to house the pressure sensor, and it allows pressures to be sensed with minimal disturbance to the locality of the sensed pressure. This latter point can be important in sensitive locations such as the eye, brain, heart, etc.

The sensed pressure is at the open end of the cannula. Static fluid pressure exhibits that pressure through the cannula and into a rigid or semi-rigid chamber surrounding the pressure sensor. Thus the pressure sensor's measurement is indifferent to pressure changes surrounding the rigid or semi-rigid chamber housing.

Inside the chamber, where saline and body fluid exist, a protective membrane transmits pressure from the liquid bodily fluid to a protective fluid encapsulating the pressure sensor. This keeps the sensitive pressure sensing device, such as a silicon membrane, from reacting with body fluids or being subject to direct biofouling.

An intraocular pressure (IOP) sensor, made in accordance with this design, can be combined with a drainage tube used to treat glaucoma. Glaucoma is excessive IOP and can lead to retinal damage and blindness. The tubes for the sensor and drainage may be separate, branched, or concentric, or some combination of the above. The drainage tube(s) may exist without a valve, may contain a passive valve, such as a check valve, or may contain an active valve, which may or may not be programmable to set at specific pressures or open according to some state that the system internal logic indicates that a valve should open or close, or to some partial open state. The drainage tube(s) may contain any combination or numbers of such valves.

Beads made of a biocompatible material, such as glass, can be incorporated with different sizes and amounts to achieve a desired flow resistance. Glass, silica, and other nonmetal beads are typically magnetic resonance imaging (MRI) compatible.

Figure 1:
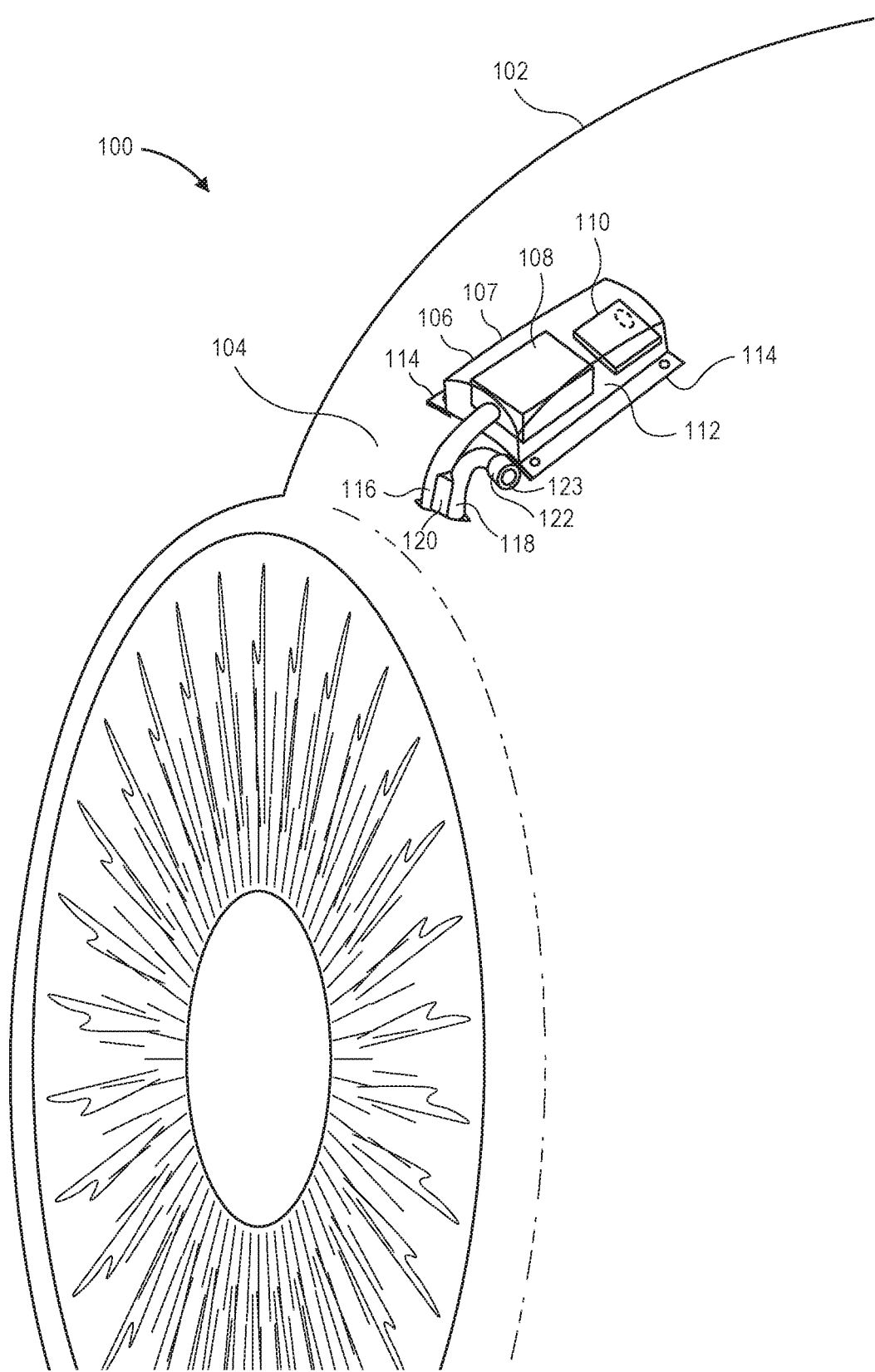
FIG. 1 illustrates a perspective view of an implanted pressure sensor device in accordance with an embodiment.

FIG. 1 illustrates a perspective view of an implanted pressure sensor device. In assembly 100, device 106 is implanted onto eye 102 at the superior temporal quadrant and underneath the conjunctiva. Some devices can be implanted at the inferior temporal quadrant as well.

Device 106 includes semi-rigid housing 107 surrounding electronic pressure sensor 108, integrated circuit (IC) 110, and flexible printed circuit board (PCT) 112. Semi-rigid housing 107 is made of shape fitting silicone rubber material. Wings 114 are integrally formed with housing 107 to provide a thin surface for sutures. A rigid or semi-rigid housing can be manufactured as a single, integrated shell, or it can be composed of multiple pieces assembled together.

Sensing cannula 116, a 23-gauge tube, runs from a chamber within housing 107 through pars plana 104 into the vitreous humor of eye 102. The cannula traverses a tiny slit that was surgically placed.

Drain cannula 118 runs side by side sensing cannula 116 through pars plana 104. Silicone rubber filler wedge 120 is shown in the triangular valley between sensing cannula 116 and drain cannula 116, which would otherwise have a figure eight, double-barrel cross section. Along with a filler wedge on the opposing valley, the filler wedge 120, sensing cannula 116, and drain cannula 118 form a racetrack, elliptical, or otherwise oval cross section. A smooth, edgeless cross section may allow the sclera to heal faster and seal better than if the tubes presented a figure eight cross section.

Flow resistor/restrictor 122 sits on proximate free end 123 of drain cannula 118. Proximate end 123 of drain cannula 118 is opposite the portion of the drain cannula that adjoins and runs parallel with sensing cannula 116 through the pars plana. Flow restrictor 122 is thus serviceable by an ophthalmologist in an outpatient, non-surgical environment.

Figure 2A:
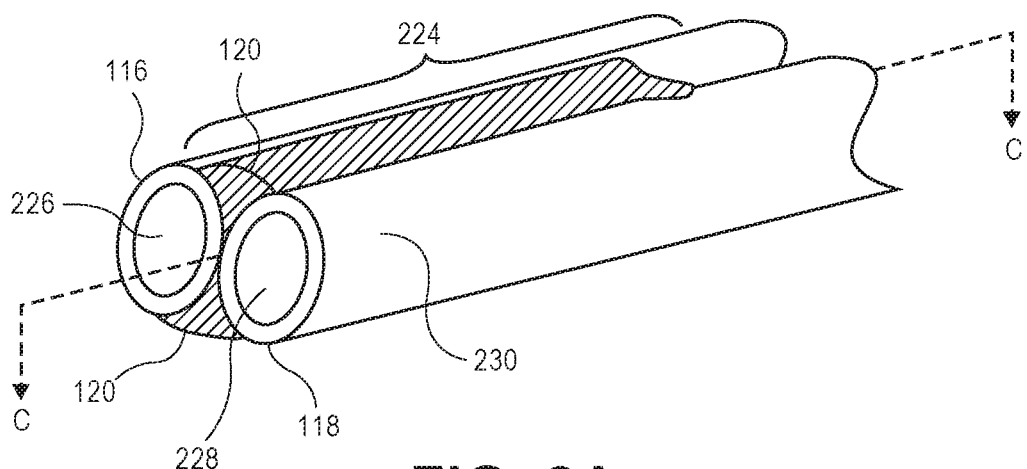
FIG. 2A illustrates a perspective view of a distal end of sensing and drain cannulas with an oval cross section in accordance with an embodiment.
Figure 2B:
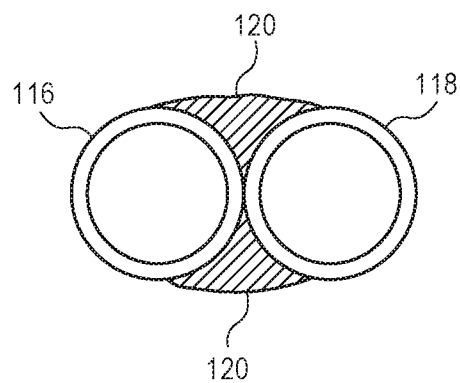
FIG. 2B illustrates an end view of the distal end in FIG. 2A.
Figure 2C:
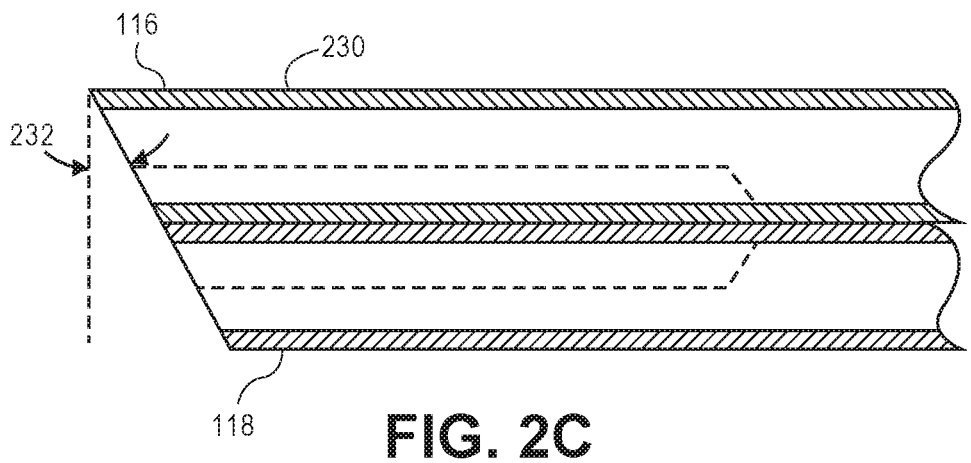
FIG. 2C illustrates a longitudinal cross-section of the distal end in FIG. 2A.

FIGS. 2A-2C illustrate a distal end 230 of sensing and drain cannulas with an oval cross section. This is the end inside the eye. The oval cross section refers to the outside diameters of the cannulas and perimeter of the wedges and not inner diameters of lumens 226 (for sensing cannula 116) and 228 (for drain cannula 118).

Sensing cannula 116 and drain cannula 118 lay side by side, adjoining each other and running parallel in portion 224. Wedges 120 fill in the indented valleys such that the cross section, as seen from the end view in FIG. 2B, is oval.

In this embodiment, end 230 is laterally slanted from sensing cannula 116 to drain cannula 118, as shown in the cross section view of FIG. 2C. The angle is shown as angle 232. This may make surgical insertion into the pars plana easier. The end could also be slanted in other planes, such as symmetrically across both cannulas, or rounded.

Figure 3A:
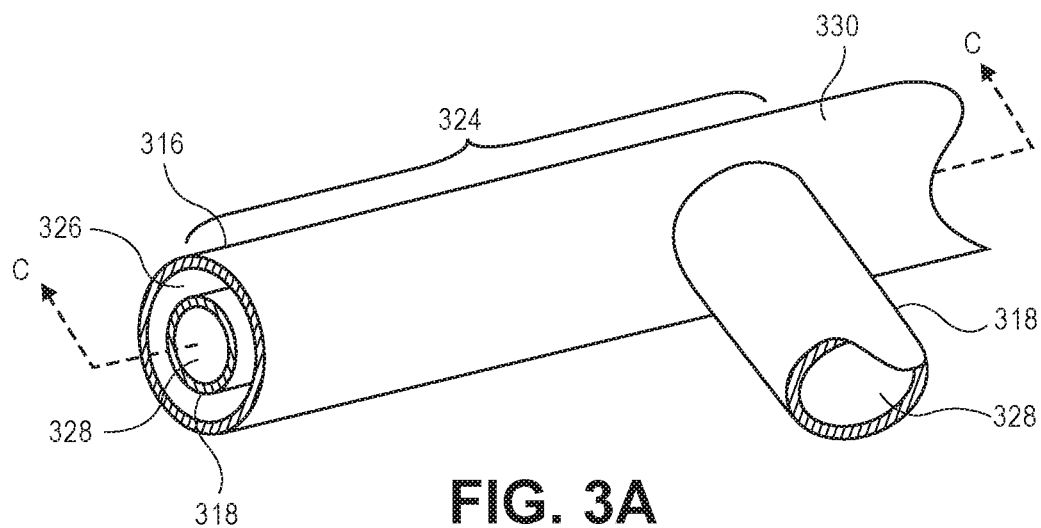
FIG. 3A illustrates a perspective view of a distal end of coaxial sensing and drain cannulas in accordance with an embodiment.
Figure 3B:
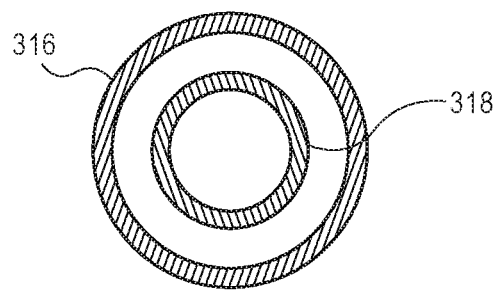
FIG. 3B illustrates an end view of the distal end in FIG. 3A.
Figure 3C:
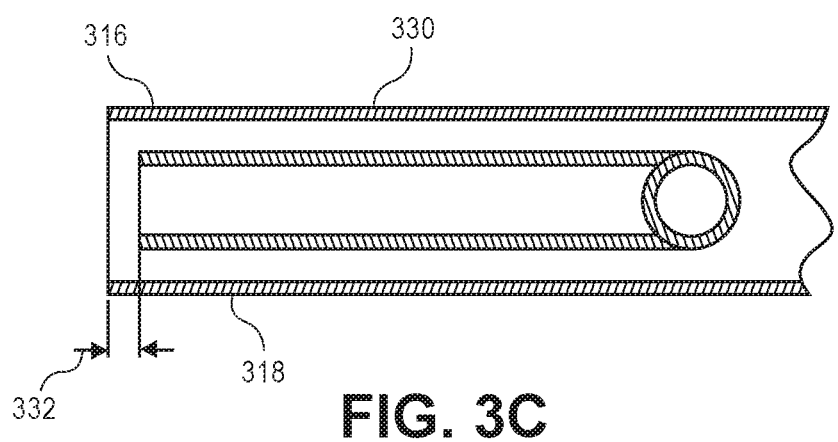
FIG. 3C illustrates a longitudinal cross-section of the distal end in FIG. 3A.

FIGS. 3A-3C illustrate distal end 330 of coaxial sensing and drain cannulas. "Coaxial" refers to the general placement of one tube within another and does not require that the cannulas are centered around a common axis. The inner tube can touch the inside of the outer tube.

Sensing cannula 316 with lumen 326 is shown as surrounding drain cannula 318 with lumen 328 in portion 324 where they adjoin and run parallel to each other. Some distance from the end, the inner cannula, here drain cannula 318, exits the outer cannula to split off. This separation can be a tee ("T") joint as shown, wye ("Y") joint, or other joint geometry.

In this embodiment, end 330 has a slight inset distance 332 of inner drain cannula 318 from the end of outer sensing cannula 316. In some embodiments, the distance may be negative. That is, the inner tube may extend beyond the end of the outer tube so that it pokes out of the outer tube. In either case, the shared space of the two cannulas presents a smooth, circular cross section circumference to the eye, which may allow the slit in the sclera heal faster and better.

In some embodiments, the drain cannula can be the outer tube and the sensing cannula be the inner tube. Triaxial tubes and greater may also be employed.

Figure 4A:
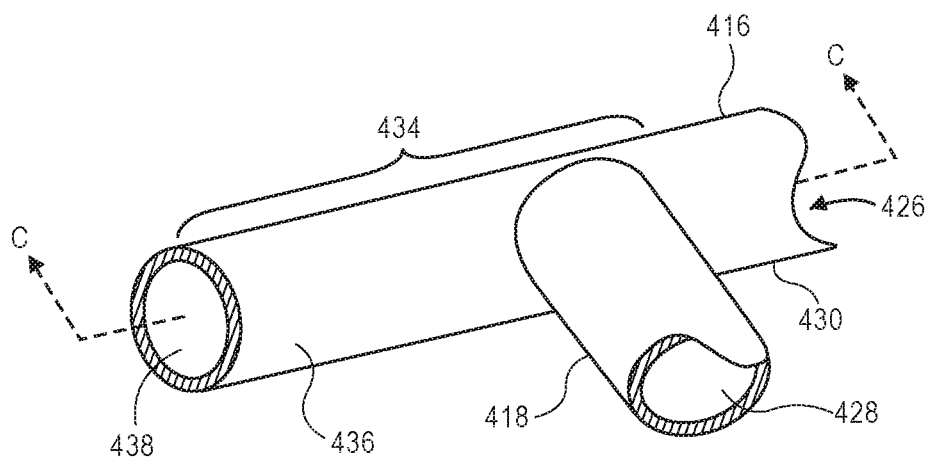
FIG. 4A illustrates a perspective view of a distal end of sensing and drain cannulas that intersect and share a common lumen in accordance with an embodiment.
Figure 4B:
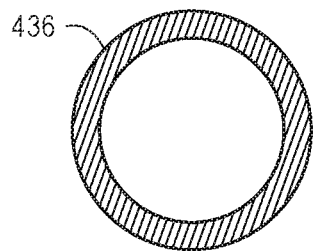
FIG. 4B illustrates an end view of the distal end in FIG. 4A.
Figure 4C:
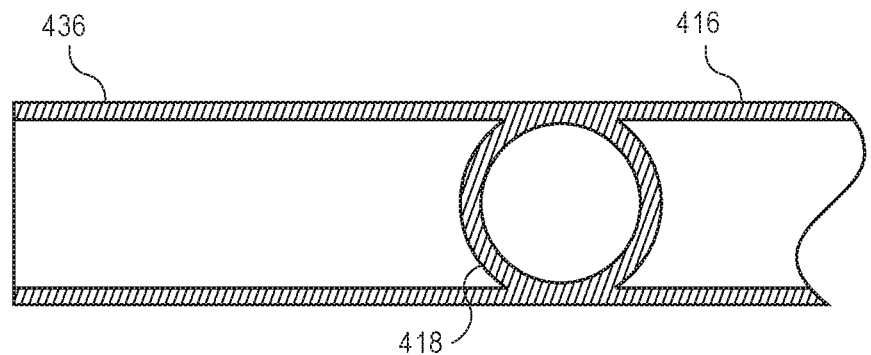
FIG. 4C illustrates a longitudinal cross-section of the distal end in FIG. 4A.

FIGS. 4A-4C illustrate distal end 430 of intersecting sensing and drain cannulas that share a common lumen.

Sensing cannula 416 with lumen 426 intersects drain cannula 418 with lumen 428. They share a common cannula 436 with common lumen 438 to its end. In portion 434, it can be said that sensing cannula 416 and drain cannula 418 adjoin and run parallel to one another by sharing their structure to form common cannula 436.

At the end, common cannula has a circular cross section, as seen in the end view of FIG. 4B. The smooth, circular cross section may promote healing.

In this embodiment, sensing cannula 416, drain cannula 418, and common cannula 436 are shown with similar diameters. In other embodiments, the cannulas may have different diameters from one another. For example, the sensing and drain cannulas can have different diameters, and/or the common cannula can have a larger (or smaller) diameter from other two cannulas.

More than one sensing cannula and more than one drain cannula can be incorporated. This allows for backup paths for sensing and draining if one tube becomes blocked. Multiple drain cannulas of a given size allows for greater drain capacity than with just one drain cannula of the size.

Figure 5:
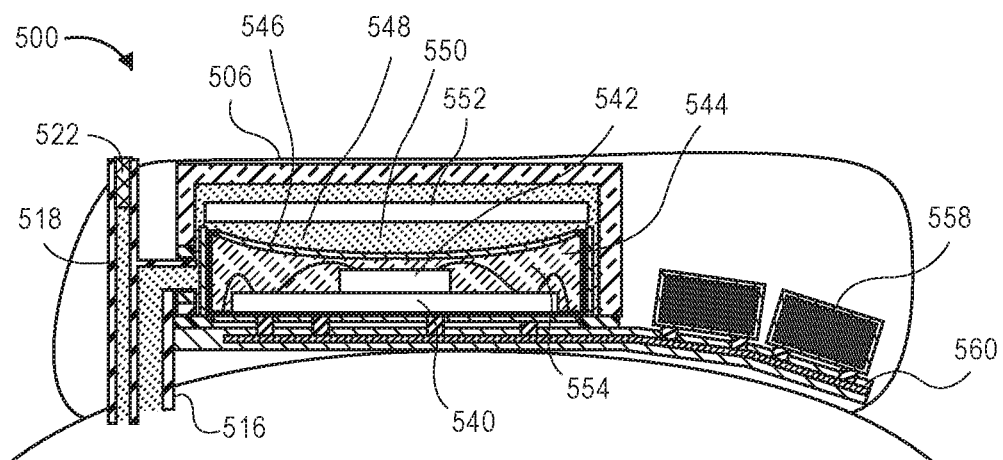
FIG. 5 illustrates an implanted pressure sensor apparatus with side-by-side sensing and drain cannulas in accordance with an embodiment.

FIG. 5 illustrates an implanted pressure sensor apparatus 500 with side-by-side sensing and drain cannulas.

Device 506 houses electronic pressure sensor 540 with pressure sensitive silicon membrane 542. Electronic pressure sensor 540 measures resistance readings and outputs them to IC 558 with a communications coil via flexible polyamide PCB 560.

Pressure sensitive silicon membrane 542 is encapsulated by oil chamber 554. Oil chamber 554 has sub-micron (0.2-1 μm) thick parylene C pliable membrane 546 on its top side. The oil chamber is filled with 100,000 centi-Stoke (cSt) biocompatible, silicon-compatible silicone oil 544. Pliable membrane 546 was manufactured by chemical vapor deposition (CVD) of parylene onto the meniscus surface of silicone oil 544 that filled the bowl-like chamber surrounding the pressure sensitive silicon membrane.

Other miniature pressure device technologies can be used instead of a piezoresistor on a silicon membrane. For example, the pressure sensitive membrane can be one side of a capacitor in which capacitance is measured. It is understood that many different pressure sensing technologies may be compatible with these designs.

Guarding thin parylene pliable membrane 546 from needle pricks is glass plate 552, which is suspended above the pliable membrane within the cured silicone housing. If a surgeon's needle accidentally pokes into the top of the device, it will be stopped by the glass plate before catastrophically poking the pliable membrane.

In the space above pliable membrane 546, opposite the side with silicone oil, is saline chamber 548. In the figure, the area above pliable membrane 546 is saline chamber 548. Saline chamber 548 is filled with saline and/or fluid 550 from the eye. The saline and fluid from the eye ideally form a continuous column through sensing cannula 516 to the inside of the eye.

Drainage cannula 518, with flow resistor/restrictor 522, enters the eye in the same hole as sensing cannula 516. As shown, the cannulas are within the silicone housing, and the end of the flow restrictor with the drainage cannula is accessible at the top of the housing. They are shaped with wedges to present an elliptical cross section to the pars plana.

Drainage and sensing cannulas can enter the housing at a tangential, normal (to the eye), or other angle in relation to the underlying PCB.

Figure 6:
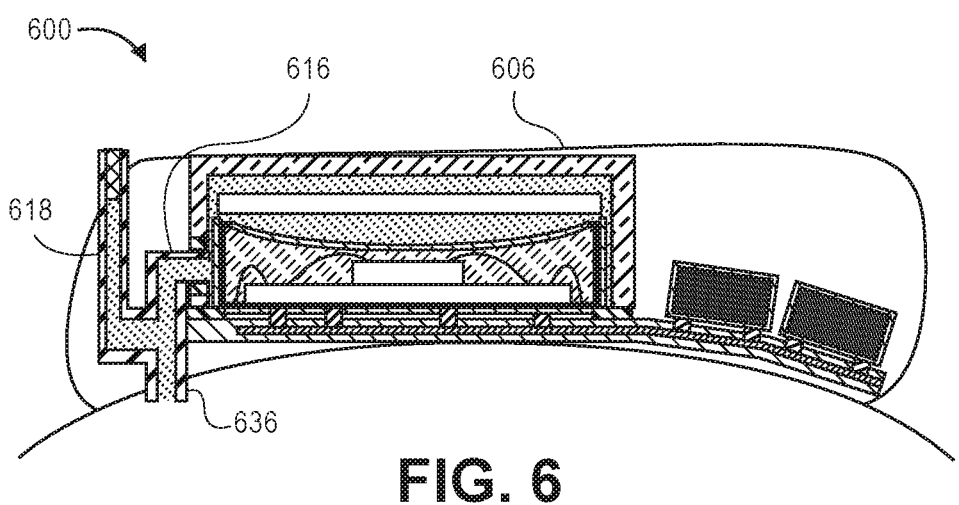
FIG. 6 illustrates an implanted pressure sensor apparatus with "T" intersecting sensing and drain cannulas in accordance with an embodiment.

FIG. 6 illustrates implanted pressure sensor apparatus 600 with coaxial sensing and drain cannulas. Device 606 includes sensing cannula 616 and drain cannula 618 that intersect. The cannulas share a common tube 636 and lumen where they enter the eye.

Figure 7:
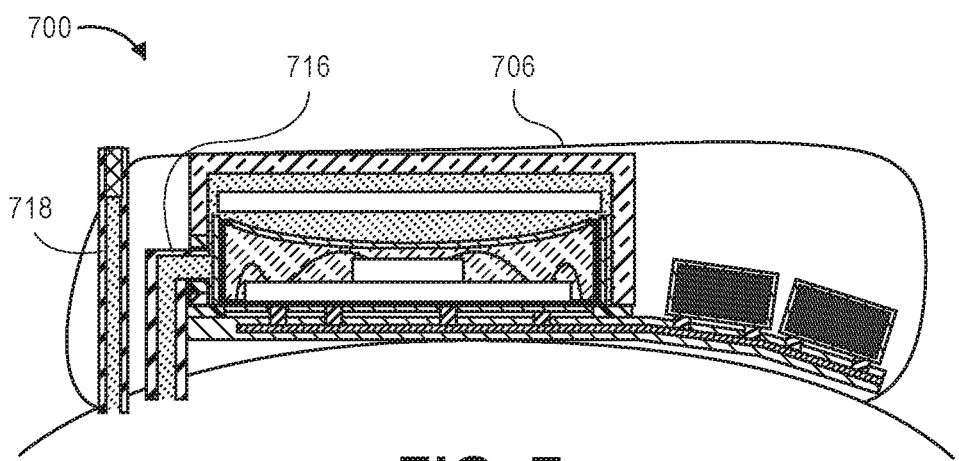
FIG. 7 illustrates an implanted pressure sensor apparatus with separated sensing and drain cannulas in accordance with an embodiment.

FIG. 7 illustrates implanted pressure sensor apparatus 700 with separated sensing and drain cannulas. Device 706 includes sensing cannula 716 and drain cannula 718 that enter the eye in different locations. The cannulas can be within the device housing as shown or exit the housing on the side before entering into the eye in separate holes.

Figure 8:
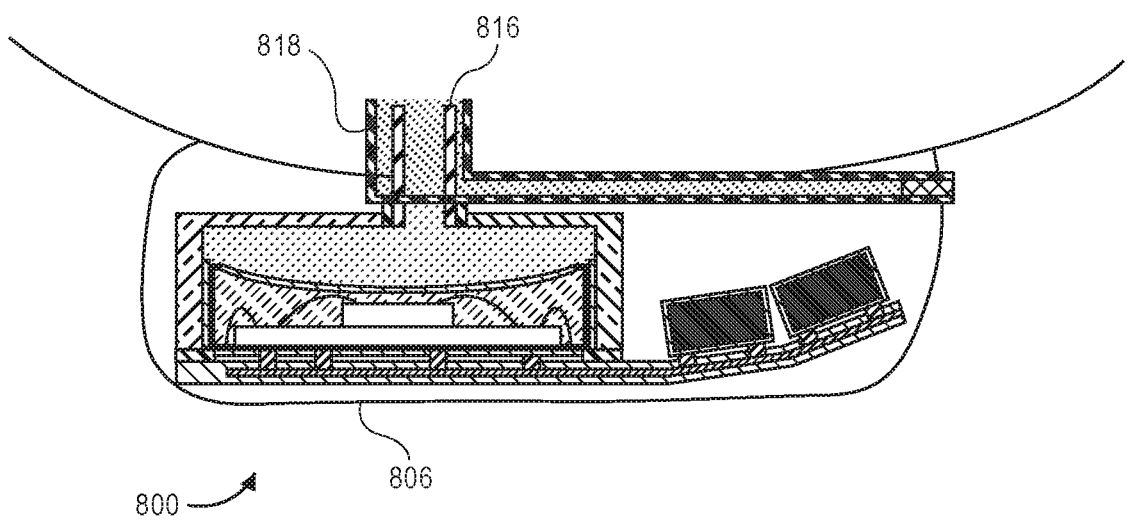
FIG. 8 illustrates an implanted pressure sensor apparatus with a sensing cannula coaxially located within a drain cannula in accordance with an embodiment.

FIG. 8 illustrates an implanted pressure sensor apparatus 800 with a sensing cannula coaxially within a drain cannula. Device 806 is mounted such that the PCB is away from the eye and sensing cannula 816 goes directly into the eye. Drainage cannula 818 extends tangentially from one end of the device and then coaxially surrounds sensing cannula 816 before they both enter the eye in one location.

Figure 9:
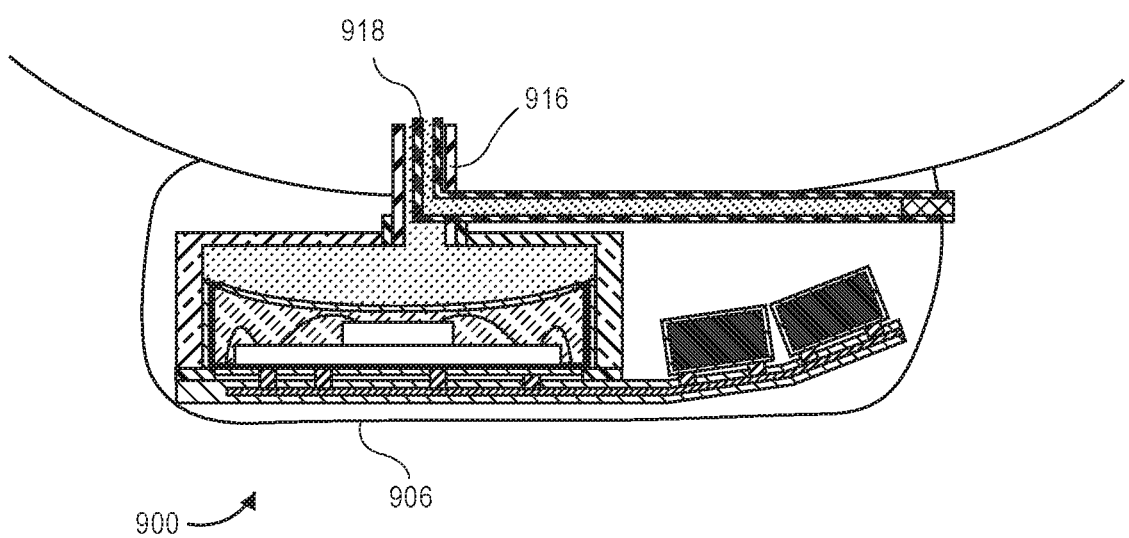
FIG. 9 illustrates an implanted pressure sensor apparatus with a sensing cannula coaxially surrounding a drain cannula in accordance with an embodiment.

FIG. 9 illustrates an implanted pressure sensor apparatus 900 with a sensing cannula coaxially surrounding a drain cannula. Device 906 is mounted similarly to that in FIG. 8 such that the PCB is opposite the eye and sensing cannula 916 extends direction into the eye. Drainage cannula 918 runs from one end of the device and then is coaxially surrounded by sensing cannula 916 before they both enter the eye in one location.

There may be one or more tubes or cannulas and/or a rigid chamber surrounding the sensing membrane such that liquid pressure at the open end of the tube may be sensed rather than the pressure immediately outside of the rigid chamber. This may be less invasive near the site of measurement. For example, a tube could mate the pressure exhibited inside a rigid chamber inside which resides the sensing membrane to the pressure inside an organ, with at least a portion of the device outside that organ. One example organ is the eye, where a tube divulges intraocular pressure to the device which resides outside the sclera. Other examples of organs whose internal pressure could be measured are the bladder, the brain, the aorta, etc. This configuration could enable the minimization of disturbance of the desired measurement location by housing the other components at another location that is advantageous to patient safety, comfort, device lifetime and performance, or some other reason.

Additional components can be added to the assemblage or packages described herein, such as temperature sensors, flow sensors, vibration, acceleration, or gyro sensors as well. Active components can also be present, such as an actuated valve, intended to change the state of the system, such as pressure, besides just sensing the environment.

Other components of a system which may be present on an implantable pressure sensor may be present. They include a wireless data transceiver, wireless power receiver, a rechargeable or non-rechargeable battery, or an application-specific integrated circuit (ASIC) chip which manages power and data. They also include external passive components like resistors and capacitors or a memory chip such as an electrically erasable programmable read-only memory (EEPROM).

The ASIC chip may be programmable to accommodate different rates of sampling, times when to sample, such as only during the day, or 24 hours a day. The ASIC chip may be programmable to change its behavior depending on multiple factors, including the rate of change of measurement, time since last measurement, time since last stored measurement, time of day and battery life remaining, and user/doctor input. The system may uplink data from its data bank to a data repository onto a server, through a personal electronic device or an application on a smartphone. The data may be time-stamped. The records for each patient may be stored cumulatively and may be updated routinely and accessed by doctors without seeing the patient.

The device may be powered by several different methods, and any or some combination of the following: photovoltaic cells, radiofrequency (near field inductive coupling, mid-field, or far-field) using an on-chip or off-chip antenna, a battery, electrostatic induction by either keeping fixed voltage or fixed charge, capacitive charge transfer for energy storing, optical power transfer, an ultrasonic energy harvester such as transduction by microelectromechanical systems (MEMS) cantilevers or lead zirconate titanate (PZT), energy harvested from other vibrations generated by the body, energy from ambient temperature gradients or infrared radiation, electrochemical or fuel cell based energy harvesting. In the case of inductive coupling, power may be provided by a coil outside. In addition, energy harvesting could also be achieved by employing metamaterials. This outside coil may reside on something worn, like a mask, for sleeping or as an attachment to glasses, or may be held or fixed to recharge for a period of time. The coil may be integrated into a pillow or device which charges the implant when the patient is laying on a bed.

Any of the features of the device may be including as separate chips or on one or more integrated chips in any combination, such as on-chip capacitors and supercapacitors for energy-storage in CMOS processing.

Devices can measure intraocular pressure (IOP) in a continuous, robust way. This is important for treating glaucoma, which may lead to blindness. Measuring IOP can verify that a drain is functioning correctly, or not, and can alert the patient and doctor if or when a drain may start to clog or malfunction, or is insufficient in preventing excessive IOP.

FIG. 10 illustrates a flow resistor with filtered or caged microbeads. Liquid within drain cannula 1018 flows to the right to flow restrictor 1022. Flow restrictor 1022 incorporates cage 1068 that holds microbeads 1064. On one side of flow restrictor 1022 holds self-sealing injection port 1066. Other flow restrictors incorporating microbeads are envisioned.

FIG. 11 illustrates flow resistor 1122 on drain cannula 1118 with step trap 1170 for microbeads 1164. The microbeads stay put in their trap without loss by virtue of their packing and the steps.

FIG. 12 illustrates flow resistor 1222 on drain cannula 1218 with a reduced inner diameter 1172 for trapping microbeads.

Both insufficient drainage and excessive drainage are problematic for medical applications where fluid needs to be drained, such as draining intraocular fluid for glaucoma. The microbeads in the flow restrictor/resistors can be made of glass or silica, among other biocompatible materials, and the bead size and quantity as well as tube diameter can be selected for the desired flow resistance per unit distance of flow resistor. The region which contains the beads can be made of silicone, glass, silicon, or other biocompatible materials. The injection port may be sealed afterwards, or it can be a self-sealing injection area in which beads can be loaded into a loading device, such as a syringe, and inserted into the trap area.

Figure 13:
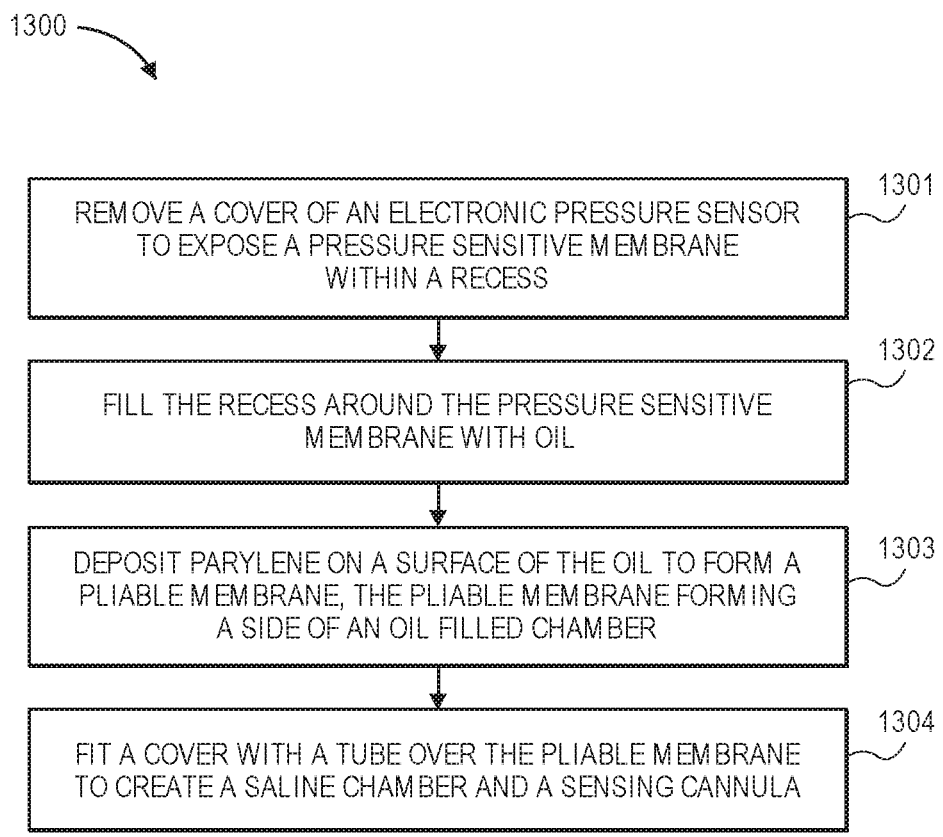
FIG. 13 is a flowchart of a process in accordance with an embodiment.

FIG. 13 is a flowchart of process 1300 in accordance with an embodiment. In operation 1301, a cover of an electronic pressure sensor is removed to expose a pressure sensitive silicon or other material membrane within a recess. In operation 1302, the recess around the pressure sensitive membrane is filled with oil. In operation 1303, parylene is deposited, by CVD, on a surface of the oil in order to form a pliable membrane, the pliable membrane forming a side of an oil filled chamber. The rest of the oil filled chamber is the recess. In operation 1304, a cover with a tube is fit over the pliable membrane to create a saline chamber and a sensing cannula.

The process can include depositing a thick layer of parylene over the electronics and oil before the thinner layer that forms the pliable membrane. The thicker layer is scraped off of the oil, more oil is added to top off the recess and minimize curvature of the meniscus, and then the second, thin layer of parylene is deposited to form the pliable membrane.

Some miniaturized pressure sensors, such as a LPS331AP or LPS25H by STMicroelectronics, can be opened from the top. For these, silicone oil is deposited into the plastic package, and the oil contained like a bowl.

Alternatively, a single circuit chip can integrate the pressure sensor, such as capacitive or piezoresistive membrane, with a wireless transceiver and/or integration with other on-chip modules or off-chip modules for compactness and reduction of number of components. This circuit chip can also be designed for subsequent encapsulation with oil and parylene to protect the pressure sensor long term.

A PCB, flexible or rigid, can connect the pressure sensor to additional components. A sufficiently rigid chamber, such as a silicone cap, can be attached around the pressure sensor to isolate the pressure from the immediate surroundings. It is made of biocompatible materials such as silicone or acrylic. A cannula mates the pressure inside the chamber to the posterior ocular chamber. The cannula will enter through the pars plana at the superior or inferior temporal quadrant. The device may be housed in shape fitting silicone, shaped by molding or some other method, and will reside under the conjunctiva. The device may also have another cannula or a branched cannula which provides drainage to relieve excessive IOP.

Although exemplary embodiments in the figures are shown with respect to ocular implants, embodiments are certainly envisioned for other areas of the body where miniaturization and minimal invasiveness is preferred, such as the brain, heart, etc. For example, a pressure sensor may be mounted outside the cranium with sensor and drain cannulas running through the skull into the brain to measure and relieve pressure.

The invention has been described with reference to various specific and illustrative embodiments. However, it should be understood that many variations and modifications may be made while remaining within the spirit and scope of the following claims.

What is claimed is:

1. An implantable pressure sensor apparatus comprising:
   an electronic pressure sensor with a pressure sensitive membrane;
   an oil chamber encapsulating the pressure sensitive membrane, the oil chamber filled with a biocompatible oil and having a pliable membrane on at least one side;
   a saline chamber on an opposite side of the pliable membrane from the oil chamber;
   a sensing cannula with a lumen extending into the saline chamber;
   a drain cannula with a portion adjoining and running parallel with the sensing cannula;
   filler wedges within valleys between the sensing cannula and the adjoining drain cannula, the filler wedges, sensing cannula, and drain cannula forming an oval cross section; and
   a flow restrictor within the drain cannula.

2. The apparatus of claim 1 wherein the filler wedges extend to an end of the adjoining drain cannula and sensing cannula.

3. The apparatus of claim 2 wherein the end is slanted.

4. The apparatus of claim 1 wherein the filler wedges comprise cured silicone rubber.

5. The apparatus of claim 1 wherein the flow restrictor is proximate a free end of the drain cannula opposite an end with the portion adjoining and running parallel.

6. The apparatus of claim 1 further comprising:
   microbeads within the flow restrictor, a packing of the microbeads configured to limit fluid flow.

7. The apparatus of claim 6 further comprising:
   an injection port on the flow restrictor configured to allow access by a needle to the microbeads.

8. The apparatus of claim 1 wherein the flow restrictor comprises a mechanical valve.

9. The apparatus of claim 1 further comprising:
   a flexible printed circuit board (PCB);
   a coil connected with the PCB;
   a wireless transmitter connected with the coil; and
   an integrated circuit (IC) configured to transmit a pressure reading from the electronic pressure sensor through the wireless transmitter and coil.

10. The apparatus of claim 1 wherein the biocompatible, silicon-compatible oil comprises silicone oil.

11. The apparatus of claim 1 wherein the pliable membrane includes parylene.

12. The apparatus of claim 1 further comprising:
   a glass plate suspended above the pliable membrane.

13. The apparatus of claim 1 wherein the saline chamber is comprised of a semi-rigid polymer.

14. An implantable pressure sensor apparatus comprising:
   an electronic pressure sensor with a pressure sensitive membrane;
   an oil chamber encapsulating the pressure sensitive membrane, the oil chamber filled with a biocompatible oil and having a pliable membrane on at least one side;
   a saline chamber on an opposite side of the pliable membrane from the oil chamber;
   a glass plate suspended above the pliable membrane;
   a sensing cannula with a lumen extending into the saline chamber;
   a drain cannula with a portion adjoining and running parallel with the sensing cannula; and
   a flow restrictor within the drain cannula.

15. The apparatus of claim 14 further comprising:
   filler wedges within valleys between the sensing cannula and the adjoining drain cannula, the filler wedges, sensing cannula, and drain cannula forming an oval cross section.

16. The apparatus of claim 15 wherein the filler wedges extend to an end of the adjoining drain cannula and sensing cannula.

17. The apparatus of claim 16 wherein the end is slanted.

18. The apparatus of claim 15 wherein the filler wedges comprise cured silicone rubber.

19. The apparatus of claim 14 wherein the flow restrictor is proximate a free end of the drain cannula opposite an end with the portion adjoining and running parallel.

20. The apparatus of claim 14 further comprising:
   microbeads within the flow restrictor, a packing of the microbeads configured to limit fluid flow.

* * * * *